United States Patent [19]

Ganias

[11] 4,041,552
[45] Aug. 16, 1977

[54] ARTIFICIAL LENS
[76] Inventor: Fotios Ganias, 4 N. Ashland St., Worcester, Mass. 01609
[21] Appl. No.: 719,672
[22] Filed: Sept. 1, 1976
[51] Int. Cl.² .............................. A61F 1/16; A61F 1/24
[52] U.S. Cl. ............................................................. 3/13
[58] Field of Search ........................................... 3/13, 1

[56] References Cited
U.S. PATENT DOCUMENTS 3,711,870  1/1973  Deitrick ...................................... 3/13
3,906,551  9/1975  Otter .......................................... 3/13
3,971,073  7/1976  Richards et al. ........................... 3/13

Primary Examiner—Ronald L. Frinks
Attorney, Agent, or Firm—Norman S. Blodgett; Gerry A. Blodgett

[57] ABSTRACT

Artificial lens for replacement of natural lens in the eye, wherein an elongated arm is provided for attaching the lens to the ciliary body and sclera and for locating the lens adjacent the iris without interfering with the operation thereof.

9 Claims, 5 Drawing Figures

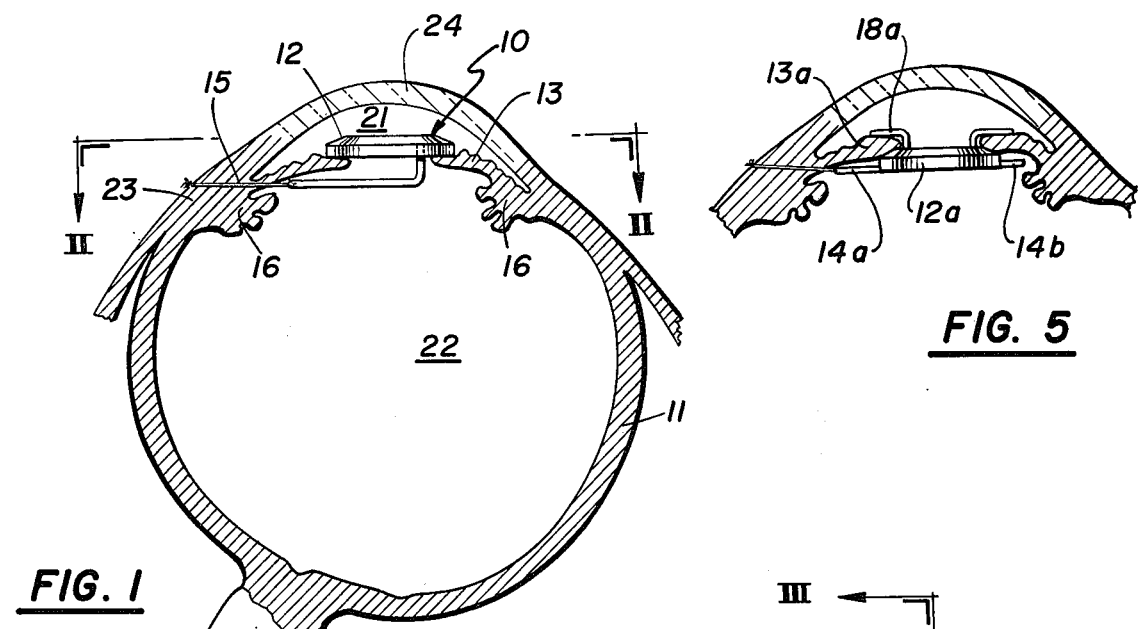
FIG. 1
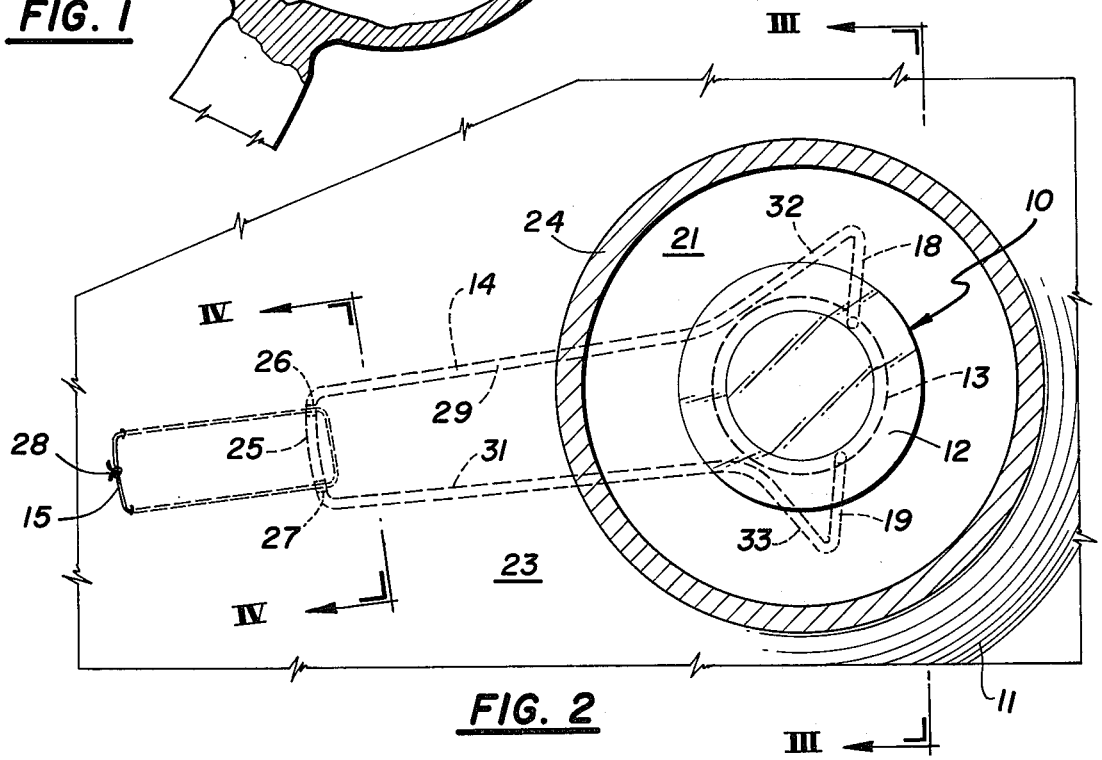
FIG. 5
FIG. 2
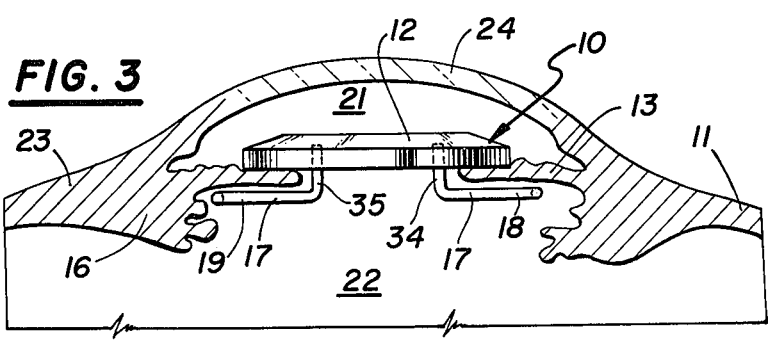
FIG. 3
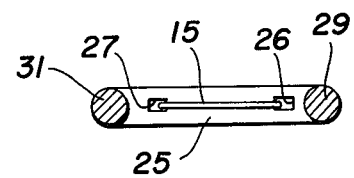
FIG. 4

ARTIFICIAL LENS

BACKGROUND OF THE INVENTION

During the operation for the removal of a cataract, it is common practice to remove the natural lens of the eye. In years past, becausse of the absence of the lens, it has been necessary to provide the patient with special eye glasses to at least partially restore his sight. These eye glasses, however, are only capable of restoring a portion of the sight and they are not entirely effective, because they present a very large magnification of the image and because they suffer from a peripheral distortion of sight. Magnification makes "binocular" vision difficult if the other eye is healthy, and the narrow angle of sight results in the so-called "tunnel vision," i.e., loss of side vision.

Besides these difficulties with cataract lenses, it has always been the desire of the medical profession to be able to replace the natural lens wih an artificial lens. Until recently the materials that were available for such lenses (such as glass) have not been compatible with the interior of the eye. In World War II, it was noted however, that, when pilots in an accident received particles of the plastic used in the aircraft windows into the interior of the eye, the particles remained there in suspension without interfering with the operation of the eye or resulting in discomfort to the pilot. As early as 1947, therefore, attempts were made to use this plastic (polymethyl methacrylate) in artificial lenses to be inserted in the eye. Although the earlier attempts were less than successful, nevertheless, as the years went by and techniques for attaching the lens were developed, the rate of success has become fairly high. Although many different designs of artificial lens have been produced, the general approach is to use wire clips or sutures on the sides of the lens which clip through the iris to hold the lens in place. Because the iris must expand and contract and because the inner edge of the iris is often frayed and less than perfect in its construction, these lenses have in many cases fallen out. Their replacement, although an office procedure, is, nevertheless, an undesirable feature of the construction. Attempts have been made to suture the clips to the iris to prevent slippage, but the movement of the iris as it expands and contracts, has a tendency to tear the sutures out. These and other difficulties experienced with the prior art devices have been obviated in a novel manner by the present invention.

It is, therefore, an outstanding object of the invention to provide an artificial lens having a high probability of success in retention.

Another object of this invention is the provision of a lens implant which is securely located adjacent the iris and, yet, which does not require a perfectly intact iris and does not inhibit the iris movement or cause it damage.

A further object of the present invention is the provision of a lens implant which can be readily applied by a surgeon of moderate skill.

It is another object of the instant invention to provide a method of applying a lens implant which method has a high probability of success.

A still further object of the invention is the provision of a surgical procedure for implanting an artificial lens, which procedure is simple in execution and reliable in result.

It is a further object of the invention to provide a lens implant support mechanism which permits the anchorage of the implant to be more physiologically suitable and allows the placement of the implant in the posterior chamber.

It is a still further object of the present invention to provide a lens implant system which gives reliable, predictable anchorage, irrespective of variations in the nature of the iris from one patient to another; it is particularly useful where the iris is not intact and has operative ability irrespective of whether sufficient iridocapsular adhesions form to support the loops of the implant.

With these and other objects in view, as will be apparent to those skilled in the art, the invention resides in the combination of parts set forth in the specification and covered by the claims appended hereto.

SUMMARY OF THE INVENTION

In general, the present invention resides in the provision of an artificial lens for use in replacing the natural lens of the eye and consists of a lens element adapted to lie adjacent the iris. A support arm is connected at one end to the lens element and extends therefrom in a plane generally parallel to the plane of the lens element. The other end of the arm is adapted to be sutured through the ciliary body and the sclera. Means is provided to hold the lens element adjacent the iris without inhibiting the operation of the iris.

More specifically, the support arm has means for suturing to the ciliary body at points which are substantially spaced about the center of the iris and of the lens to prevent tipping of the lens. Two wire elements are located on opposite sides of the lens element and are spaced a substantial distance from the surface of the lens element, so that the lens element resides on one side of the iris, while the wire elements reside on the other side. The support arm is a loop of wire whose ends are connected to the lens elements, the loop being generally U-shaped with the lens element located at the open end and the suture points located in apertures at two remote corners. The suture passes through the ciliary body and also through the sclera, so that it can be tied on the outer surface of the sclera or conjunctiva.

BRIEF DESCRIPTION OF THE DRAWINGS

The character of the invention, however, may be best understood by reference to one of its structural forms, as illustrated by the accompanying drawings, in which:

FIG. 1 is a horizontal sectional view of a human eye, showing an artificial lens incorporating the principles of the present invenion, FIG. 2 is a sectional view taken on the line II—II of FIG. 1, FIG. 3 is a sectional view of the invention taken on the line III—III of FIG. 2, FIG. 4 is a sectional view of the invention taken on the line IV—IV of FIG. 2, and FIG. 5 is a sectional view of an eye showing in use a modified form of the invention.

DESCRIPTION OF THE PREFERRED EMBODIMENT

Referring first to FIG. 1, which best shows the general features of the invention, it can be seen that the artificial lens 10 is shown in use in a human eye 11. The lens is shown as associated with the anterior chamber 21 lying between the cornea 24 and the iris 13. A suture 15 is shown as extending from the lens and passing through the ciliary body 16 and the sclera 23.

In FIG. 2 it can be seen that a lens element 12 lies in the anterior chamber 21 and is provided with a support arm 14 which is connected at one end to the lens element and extends therefrom in a plane generally parallel to the plane of the lens element. The other end of the arm is adapted to be attached by means of a suture 15 to the ciliary body 16. Means, including wire elements 18 and 19 are provided for holding the lens element 12 adjacent the iris 13 without inhibiting its operation. The support arm 14 is provided with apertures 26 and 27 through which the suture 15 passes for connecting it to the ciliary body and sclera at points which are substantially spaced about the center of the iris to prevent tipping of the lens element.

As is obvious in FIG. 3, the two wire elements 18 and 19 reside in the posterior chamber 22 and constitute the means 17 for holding the lens element adjacent the iris. They are located on opposite sides of the lens element 12 and are spaced a substantial distance from the bottom surface of the lens element where it comes in contact with the iris, so that the lens element resides on one side of the iris (in the anterior chamber), while the wire elements reside on the other side of the iris (in the posterior chamber).

The support arm 14 is a loop of wire which, in the preferred embodiment is platinum, whose ends are connected to the lens element. The loop is generally U-shaped with the lens element located at the open end and the suture points located at two remote corners. In the preferred embodiment, the lens element is formed of a polymethyl methacrylate which is substantially free of the monomer. In the preferred embodiment, the lens element is located in the anterior chamber 21 and the suture 15 passes through the ciliary body and the sclera 23 and is tied on the outer surface thereof in a knot 28.

FIGS. 2 and 3 show that the arm 14 is a loop of rod-like material with a generally straight portion 25 extending at a right angle to an imaginary line connecting the center of the lens element 12 to the straight portion. The straight portion extends an equal amount on either direction from the said imaginary line and aperture 26 is formed in the straight portion adjacent the end thereof at one side and an aperture 27 at the other end. As has been stated, the suture 15 extends through the aperture, through the ciliary body 21 and through the sclera 23 and is tied on the exterior of the sclera. In other words, the loop of the arm 14 is generally U-shaped with two straight parallel legs 29 and 31 joined by the bight or straight portion 25 remotely of the lens element 12. The bight is provided with the substantially-spaced apertures for suturing.

The free ends of the legs 29 and 31 are connected to inclined intermediate members 32 and 33, respectively, which, in turn, are connected to generally transversely-extending guide elements 18 and 19, respectively. The ends of the guide elements 18 and 19 are provided with vertical risers 34 and 35, respectively, the upper ends of which are fastened to the lens element 12.

FIG. 4 shows particularly well the nature of the apertures 26 and 27 and the manner in which the suture 15 passes through them in order to fasten the end of the arm 14 at the spaced points that are defined by the apertures 26 and 27.

The operative procedure for replacing the natural lens of the eye which the artificial lens 10 will now be readily understood in view of the above description. First, the natural lens (which lies in the posterior chamber 22 at the rear of the iris) is removed surgically by means of an incision through the limbus, i.e., the transitional zone between the cornea and the sclera. Through the incision thus made, it is possible then to place the artificial lens in position with the lens element 12 in the anterior chamber 21 adjacent the iris 13. The arm 14 has been inserted through the pupil so that it now lies in the posterior chamber 22 rearwardly of the iris. At the same time, it is positioned so that the holding means 17, consisting of the wire elements 18 and 19, lies in the posterior chamber against the rearward surface of the iris 18. The gap between the wire elements 18 and 19 and the surface of the lens element 12, as it engages the iris, is maintained of a sufficient size to hold the lens in place without inhibiting the normal opening and closing of the iris. Furthermore, the risers 34 and 35 are located close enough together so that when the iris is in its most contracted state, they do not interfere with its operation.

With the lens element 12 in place in the anterior chamber, the arm 14 extends radially of the center of the iris into engagement with the ciliary body 16. In the preferred embodiment, the straight portion 25 of the arm lies in the corner between the ciliary muscle and the base of the iris. In this position the surgeon performs a peripheral iridectomy that gives him an opening through which he can manipulate the suture 15 through the sclera 23, through the ciliary body 16, and through the aperture 27. From there the suture passes around the arm and outwardly again through the aperture 26, the ciliary body 16, and the sclera 23 to the outside. Loose ends are then tied in the knot 28, which knot may be hidden under a flap of sclera or of conjunctiva where it cannot be seen.

The advantages of the present invention will now be readily understood in view of the above description. Because the suture points defined by the apertures 26 and 27 are widely spaced, they prevent the lens from moving relative to the rest of the eyeball despite the expansion and contraction of the iris in its normal operation and the movement of the eyeball in various ways. This effect of tying down the lens firmly to a fixed base is reinforced by the fact that the suture passes through the ciliary body and the sclera which are relatively tough fixed elements in the eyeball and are not subject to expansion and contraction. This makes the effect of applying the lens to the human eye much more predictable and avoids the use of the delicate and sometimes damaged iris as a support member. It is particularly important, since the iris apparently varies from patient to patient. Furthermore, with the present invention there need be no concern as to whether sufficient iridocapsular adhesions form to support the loops of the implant.

In FIG. 5 the lense element 12a lies in the posterior chamber, while support 18a on the anterior side of the iris 13a. The arm 14a is sutured to the ciliary body and the sclera at one side of the iris, while another arm 14b extends to the other side.

In a commercial version of the invention, the lens element 12 is formed of polymethyl methacrylate with very little of the monomer present. The lens element is of plano-convex shape and has a 5mm. diameter with a central thickness from 0.5 to 0.6mm. The loop or arm 14 is formed of platinum iridium and has a length of 5.75mm. from the center of the lens 12 to the straight portion 25 of the loop. It is formed of a rod material which is from 0.15 to 0.2mm. in diameter. In the preferred embodiment, where the loop touches the ciliary body, the loop may be thickened by 0.6 to 1mm., so that the apertures 26 and 27 will fit best. In this embodiment the apertures 26 and 27 were located 2mm. apart. The arms of wire elements 18 and 19 which lie against the iris have an overall length of 4mm. from the center of the lens. The overall length of these arms from tip to tip is 9.75mm. with a clearance between them of 0.5 to 0.75mm.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Artificial lens for application to the eye after the natural lens has been removed, comprising
   a. a lens element adapted to lie adjacent the iris, and
   b. a support arm connected at one end to the lens element and extending generally radially thereof, the other end of the arm having means for suturing it to the ciliary body and sclera at two substantially-spaced points equidistant from the center of the iris to prevent tipping of the lens element, the support arm being a loop of wire whose ends are connected to the lens element, the loop being generally U-shaped with the lens element located at the open end and the suture points located at two remote corners.

2. Artificial lens as recited in claim 1, wherein the lens element is formed of a polymethyl methacrylate which is substantially free of the monomer.

3. Artificial lens as recited in claim 2, wherein the lens element is sized and shaped for location in the anterior chamber.

4. Artificial lens as recited in claim 3, wherein a suture extends from said remote corner points and is adpated to pass through the sclera and be tied on the outer surface thereof.

5. Artificial lens for application to the eye after the natural lens has been removed, comprising
   a. a lens element adapted to lie adjacent the iris,
   b. a support arm connected at one end to the lens element and extending generally radially thereof, the other end of the arm having means for suturing it to the ciliary body and sclera at two substantially-spaced points equidistant from the center of the iris to prevent tipping of the lens element, the arm being a loop of rod-like material with a generally straight portion extending at a right angle to an imaginary line connecting the center of the lens element, the straight portion extending equal amounts in either direction from the said imaginary line and spaced apertures formed in the straight portion adjacent the ends thereof, and
   c. a suture adapted to extend through the apertures and through the ciliary body and the sclera and adapted to be tied on the exterior of the sclera.

6. Artificial lens for application to the eye after the natural lens has been removed, comprising
   a. a lens element adapted to lie adjacent the iris, and
   b. a support arm connected at one end to the lens element and extending generally radially thereof, the other end of the arm having means for suturing it to the ciliary body and sclera at two substantially-spaced points equidistant from the center of the iris to prevent tipping of the lens element, the support arm being a loop of wire whose ends are connected to the lens element, the loop being generally U-shaped with two straight parallel legs joined by a bight located remote from the lens element, the bight being provided with substantially-spaced means for suturing, the free ends of the legs being connected to inclined intermediate members which in turn are connected to generally transversely-extending guide elements at the ends of which are vertical risers the upper ends are fastened to the lens element.

7. Operative procedure for replacing the natural lens of the eye with an artificial lens, comprising the steps of
   a. removing the natural lens,
   b. placing the articial lens in position adjacent the iris, and
   c. suturing the artificial lens to the eye by use of a suture that passes through the ciliary body and the sclera, the suture passing through the sclera and ciliary body at substantially spaced points which are equidistant from the center of the iris, but located at one side only of the artificial lens, so that the lens does not interfere with the normal operation of the iris.

8. Operative procuedure as recited in claim 7, wherein the lens is guided to the iris to maintain the lens against the iris without preventing the iris from opening and closing.

9. Artificial lens for application to the eye after the natural lens has been removed, comprising
   a. a lens element adapted to lie adjacent the iris,
   b. a support arm connected at one end to the lens element and extending generally radially thereof, the other end of the arm having means for suturing it to the ciliary body and sclera at two substantially-spaced points equidistant from the center of the iris to prevent tipping of the lens element, and
   c. means provided for holding the lens element in position adjacent the iris without inhibiting the operation of the iris, the said holding means includes two wire elements located on opposite sides of the lens element and spaced a substantial distance from the surface of the lens element, so that the lens element is adapted to reside on one side of the iris while the wire elements are adpated to reside on the other side.

* * * * *